United States Patent [19]

Gaffar et al.

[11] Patent Number: 5,034,383

[45] Date of Patent: * Jul. 23, 1991

[54] INACTIVATION OF BACTERIAL ENDOTOXINS USING PEROXY-DIPHOSPHATE COMPOOUNDS

[75] Inventors: Abdul Gaffar, Somerset; Edward J. Coleman, Piscataway, both of N.J.

[73] Assignee: Colgate-Palmolive Company, Piscataway, N.J.

[*] Notice: The portion of the term of this patent subsequent to Jul. 2, 2008 has been disclaimed.

[21] Appl. No.: 323,190

[22] Filed: Mar. 13, 1989

Related U.S. Application Data

[63] Continuation of Ser. No. 851,915, Apr. 14, 1986, abandoned, which is a continuation-in-part of Ser. No. 768,394, Aug. 22, 1985, abandoned.

[51] Int. Cl.$^5$ .................... A61K 31/70; A61K 31/66; A61K 33/42
[52] U.S. Cl. ........................ 514/47; 514/48; 514/52; 514/76; 514/103; 514/921; 424/601; 424/604; 424/606
[58] Field of Search ............... 424/53, 57, 681, 604, 424/606; 514/47, 48, 52, 76, 103, 921

[56] References Cited

U.S. PATENT DOCUMENTS

| | | | |
|---|---|---|---|
| 4,041,149 | 8/1977 | Gaffar et al. | 424/57 |
| 4,177,258 | 12/1979 | Gaffar et al. | 424/49 |
| 4,183,915 | 1/1980 | Gaffar et al. | 424/52 |
| 4,273,759 | 6/1981 | Gaffar et al. | 424/54 |
| 4,309,410 | 1/1982 | Gaffar | 424/57 |
| 4,430,325 | 2/1984 | Gaffar et al. | 424/128 |
| 4,431,631 | 2/1984 | Clipper et al. | 424/53 |
| 4,537,765 | 8/1985 | Gaffar et al. | 424/53 |
| 4,537,778 | 8/1985 | Clipper et al. | 424/53 |
| 4,547,361 | 10/1985 | Steltenkamp et al. | 424/49 |

OTHER PUBLICATIONS

Textbook of Medicine; 16th Ed. (1982), p. 1336; Cecil.

*Primary Examiner*—Glennon H. Hollrah
*Assistant Examiner*—Gary E. Hollinden
*Attorney, Agent, or Firm*—Robert L. Stone; Murray M. Grill

[57] ABSTRACT

Bacterial endotoxins are inhibited by a non-toxic, water-soluble, pharmaceutically acceptable peroxydiphosphate compound in contact with bacterial endotoxin.

6 Claims, No Drawings

INACTIVATION OF BACTERIAL ENDOTOXINS USING PEROXY-DIPHOSPHATE COMPOOUNDS

This application is a continuation of application Ser. No. 851,915, filed Apr. 14, 1986 now abandoned which application is a continuation-in-part of application Ser. No. 768,394, filed Aug. 22, 1985 now abandoned.

Endotoxins are complex macromolecules containing lipid, carbohydrate and protein. They are mainly found in the surface of gram negative organisms and are usually referred to as lipopolysaccharides. These macromolecules are toxic to the host and can be fatal. For instance, they can cause severe hypotensive shocks, and also elicit a variety of toxic reactions in the body including bone resorption. In the mouth, endotoxins have been implicated as a major factor in the inflammation of gum tissues and in localized bone loss such as alveolar bone loss.

Theoretically, compounds which release oxygen could inactivate endotoxins. However, due to the quickness with which many oxygen-evolving compounds release oxygen, they generally have little effect in controlling endotoxin growth. Those compounds which release oxygen more slowly could control endotoxin effect. However, their effectiveness is generally limited in that the conditions of oxygen-release do not correspond to the conditions prevailing in the body.

As described in commonly assigned U.S. patent application Ser. No. 726,545, filed Apr. 24, 1985, warm blooded mammals, such as from rodents, up to and including humans have alkaline phosphatase or acid phosphatase in their bodies. Peroxydiphosphate compounds possess the property of slow release of oxygen. The amount of oxygen which they release is one-tenth the amount released by hydrogen peroxide. Only about 50% of their active oxygen is released in 20 hours at 25° C. in the presence of alkaline phosphatase or acid phosphatase.

Peroxydiphosphate compounds (PDP) release hydrogen peroxide slowly in the presence of phosphatase enzymes in accordance with the following equation:

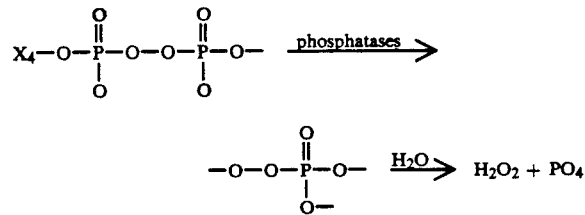

wherein X is a non-toxic pharmaceutically acceptable cation or completes an organic ester moiety. Phosphatase to break down the peroxydiphosphate is present in saliva as well as in plasma, intestinal fluids and white blood cells.

It has been observed that bacterial endotoxin also reacts with intact PDP. This reaction occurs independently of the presence of phosphatases; that is, it occurs outside of the body of a warm blooded animal too. However, quite importantly, even in the presence of phosphatase, the reaction also occurs when warm blooded mammalian animals are treated with PDP in accordance with the present invention. It is desirable to provide a regimen whereby treatment continues until endotoxins are inactivated.

It is an object of this invention to deactivate endotoxins and thereby inhibit their toxic effects, such as inflammation, bone resorption and hypotensive shocks.

Other objects of this invention will be apparent from consideration of the following specification.

In accordance with certain of its objects, this invention relates to a method for inhibiting hypotensive shock and localized bone resorption caused by bacterial endotoxin which comprises introducing a non-toxic water-soluble, pharmaceutically acceptable peroxydiphosphate compound into contact with endotoxin to cause inactivation of said bacterial endotoxin.

A procedure for evidencing inactivation of endotoxin is by overcoming induction of generation of a factor which is chemotactic to polymorphonuclear leukocytes, hereinafter called "PMN". Such a factor can be assessed in accordance with the Boyden chemotaxis method wherein white blood cells of a rabbit are attracted (chemotaxis) by endotoxin induced factor generated in the area. In the Boyden method, when a bacterial endotoxin lipopolysaccharide is incubated with a serum from a mammalian, what occurs is:

$$\text{Serum and Endotoxin} \xrightarrow[\text{temperature for 1 hr.}]{\text{Incubated at body}} \text{chemotactic factors for PMN}$$

The chemotaxis phenomenon is studied using Boyden chambers as described by Cates et al, "Modified Boyden Chamber Method for Measuring PMN Chemotaxis" in *Leukocyte Chemotaxis, Methods, Physiology and Clinical Application*, edited by Gallin and Quie, Raven Press, N.Y., 1978, pages 67-71. When endotoxin induces chemotaxis as in the present invention, the percentage of inhibition can be quantified using the Boyden chemotaxis test.

Endotoxin material can be introduced into the body of a warm blooded animal through its presence in the surfaces of gram negative microorganisms, such as *Actinobacillus actinomycetemcomitens* (A.a), *Escherichia coli* (E. coli), *Bacteroides melanenogenicus* (B. mel) and *Salmonella typhi* (S. typhi).

Oral endotoxin isolated from A. a. is toxic to avelolar bone. Non-oral endotoxin purified from E. coli can prove fatal to the host.

Other known procedures for inhibiting endotoxin formation are done using resorption in a bone culture medium; a chick embryo lethality test can also be used.

The toxic reaction is effectively inhibited by treating endotoxin in situ in a warm blooded host with an inhibiting-effective amount of non-toxic, water-soluble pharmaceutically acceptable peroxydiphosphate compound. The peroxydiphosphate reacts with the endotoxin in the body as an intact molecule, while inactivating the peroxydiphosphate compound. Since the endotoxin is inactivated, it is apparent that endotoxin reacts with the peroxydiphosphate.

Generally, about 0.1-7% of peroxydiphosphate compound in a pharmaceutical carrier, such as in solution is effective in a regimen dosage of about 0.2-14 mg per kg body weight. Inhibition effectiveness can be evidenced by reduced endotoxin effect and is quantified on the basis of inhibited chemotaxis to PMN.

Typical non-toxic, water-soluble pharmaceutically acceptable peroxydiphosphate compounds are the alkali metal salts (e.g. lithium, sodium and potassium), alkaline earth metal salts (e.g. magnesium, calcium and strontium) and zinc, tin and quaternary ammonium salts, as well as $C_{1-12}$ alkyl, adenylyl, guanylyl, cytosylyl and thymylyl esters. Alkali metal, particularly potassium salt is preferred from among the inorganic cations. The tetrapotassium peroxydiphosphate is a stable, odorless, finely divided, free-flowing, white non-hygroscopic crystalline solid having a molecular weight of 346.35 and an active oxygen content of 4.6%.

Tetrapotassium peroxydiphosphate is 47-51% water-soluble at 0°-61° C., but insoluble in common solvents such as acetonitrile, alcohols, ethers, ketones, dimethyl formamide dimethyl sulfoxide, and the like. A 2% aqueous solution has a pH of about 9.6 and a saturated solution thereof a pH of about 10.9. A 10% solution in water at 25° C. showed no active oxygen loss after four months; and at 50° C. a 10% solution showed an active oxygen loss of 3% in 6 months.

From among the organic compounds those providing hydrophobic properties such as $C_{1-12}$ alkyl radical and those which facilitate the rapid uptake of peroxydiphosphate moiety by the cells, such as adenylyl, guanylyl, cytosylyl, and thymylyl, esters are preferred.

Peroxydiphosphate compound may be administered orally or systemically to inhibit endotoxins in the oral cavity or other parts of the body.

Pharmaceutical carriers suitable for oral ingestion are coated tablets composed of material which resists breakdown by gastric acids in the stomach pH (about 1-3) since peroxydiphosphate would be inactivated by such gastric acids. Rather, the carriers, with tableted granules of the peroxydiphosphoric acid salt solid material therein, are dissolved by intestinal fluids which have a higher pH (about 5.5-10) and do not inactivate the peroxydiphosphate, leaving it subject to enzymatic action by phosphatase present in humans or other warm blooded animals. A desirable tablet coating solution is composed of a fatty acid ester such as N-butyl stearate (typically about 40-50, preferably about 45 parts by weight), wax such as carnuba wax (typically about 15-25, preferably about 20 parts by weight), fatty acid such as stearic acid (typically about 20-30 parts, preferably 25 parts by weight) and cellulose ester, such as cellulose acetate phthalate (typically about 5-15, preferably about 10 parts by weight) and organic solvent (typically about 400-900 parts). Other desirable coating materials include shellac and copolymers of maleic anhydride and ethylenic compounds such as polyvinyl methyl ether. Such coatings are distinct from tablets which are broken down in the oral cavity in which the tablet material typically contains about 80-90 parts by weight of mannitol and about 30-40 parts by weight of magnesium stearate.

Tabletted granules of the peroxydiphosphate salt are formed by blending about 30-50 parts by weight of the peroxydiphosphate salt with about 45-65 parts by weight of a polyhydroxy sugar solid such as mannitol and wetting with about 20-35 parts by weight of a polyhydroxy sugar compound solution such as sorbitol, screening to size, blending with about 20-35 parts by weight of a binding agent such as magnesium stearate and compressing the granules into tablets with a tablet compressing machine. The tabletted granules are coated by spraying a foam of a solution of the coating material thereon and drying to remove solvent. Such tablets differ from dental tablets which are typically compressed granules without a special protective coating.

An effective dosage of administration of peroxydiphosphate with a prescribed regimen, when administration is by oral ingestion, is about 0.1-6g, per/kg of body weight daily; when administration is systemic, such as by intramuscular, intraperitoneal or intravenous injection, the dosage is about 0.1-2 g. per/kg of body weight daily.

Physiologically acceptable pyrogen-free solvents are suitable carriers for use in the art-recognized manner for systemic administration. Saline solution buffered with phosphate to a physiological pH of about 7 to 7.4 is the preferred carrier for systemic administration. Such solvents are distinct from water-humectant vehicles typically used in dentifrices. Such solution is typically prepared by sterilizing deionized distilled water, checking to insure non-pyrogenicity using the Limulus amebocyte lysate (LAL) test described by Tsuji et al in "Pharmaceutical Manufacturing", October, 1984, pages 35-41, and then adding thereto a phosphate buffer (pH e.g. about 8.5-10) made in pyrogen free sterile water and about 1-100 mgs. peroxydiphosphate compound derivative and sodium chloride to a concentration of about 0.5-1.5% by weight. The solution can be packed in vials for use after being resterilized by passing through a micropore filter. As alternatives, other solutions such as Ringer's solution containing 0.86% by weight sodium chloride, 0.03% by weight potassium chloride and 0.033% by weight calcium chloride may be used.

The following examples illustrate the ability of peroxydiphosphate (PDP) compound to inhibit chemotaxis induced by endotoxin generated factor in serum and to inhibit endotoxin toxicity to bone.

EXAMPLE 1

PMN are obtained from the peritoneal cavities of adult New Zealand white rabbits 12 hours after intraperitoneal injections of 200 ml of solution containing 0.2% glycogen in sterile isotonic saline (0.85% NaCl). The cells (PMN) are purified from the exudate obtained from rabbit peritoneal cavity and purified as described by Taichman et al (Arch. Oral Biol. 21 p. 257, 1976). Bacterial endotoxin purified from E. Coli obtained from Associates of Cape Cod Inc. Woods Hole, Maine, is pre-treated with different concentrations of PDP (tetrapotassium salt) at 37° for 1 hour. The chemotaxis assay is then run with treated and untreated endotoxins using Boyden Chamber as described above. The data are summarized in Tables 1 and 2.

TABLE 1

| | Treatment | Chemotaxis-Mean Number of PMN Migrating + S.D. | Percent Reduction in Chemotaxis |
|---|---|---|---|
| 1. | Control++ | 139 ± 4.2 | |
| 2. | Serum+++ and 1 nanogram/ml Endotoxin | 343.0 ± 36.7 | |
| 3. | 0.5% PDP and serum+++ | 142.5 ± 12.0 | |
| 4. | Endotoxin (1 ng/ml) pretreated with 0.5% PDP and serum++ | 188.0 ± 18.4 | 44 compared to 2 |
| 5. | Endotoxin (0.5 ng/ml pretreated with 0.5% | 154.0 ± 2.8 | 56% compared to 2 |

TABLE 1-continued

| | Treatment | Chemotaxis- Mean Number of PMN Migrating + S.D. | Percent Reduction in Chemotaxis |
|---|---|---|---|
| 6. | PDP and serum++ Endotoxin (0.25 ng/ml) pre-treated with 0.5% PDP and serum++ | 138.5 ± 2.8 | 60% compared to 2 |

+. S.D. = standard deviation
++medium = Earl's solution containing 10% bovine serum albumin
+++serum = human serum (normal)

The results in Table 1 indicate that endotoxin as expected, induces a great release of a factor which increased chemotaxis of PMN (#2 treatment); PDP (0.5%) has no effect on PMN (#3); and endotoxins pre-treated with PDP, have chemotactic activity of the toxin significantly reduced (treatments 4, 5 and 6). These data indicate that a treatment of endotoxin with PDP, deactivates the biological effect of the toxin.

EXAMPLE 2

Table 2 shows data obtained with further Boyden Chamber Tests as in Example 1 PDP is employed as the tetrapotassium salt.

TABLE 2

| | Treatment | Chemotaxis- Mean Number of PMN Migrating + S.D. | Percent Reduction in Chemotaxis |
|---|---|---|---|
| 1. | Control medium (as in Example 1) | 136.5 ± 6.3 | |
| 2. | Endotoxin 1 ng/ml and serum+ | 329.0 ± 39.5 | |
| 3. | PDP 0.5% and serum+ | 139.5 ± 4.9 | |
| 4. | Endotoxin (1 ng/ml) pre-treated with 0.5% PDP and serum+ | 188.0 ± 9.8 | −43.0% |
| 5. | Endotoxin (1 ng/ml) pre-treated with 0.25% PDP and serum+ | 206.5 ± 17.6 | −37% |
| 6. | Endotoxin (1 ng/ml) pre-treated with 0.1% PDP and serum+ | 231.0 ± 17.6 | −30% |

+serum as in Example 1.

The data in above table show effective concentration of PDP of at least as little as 0.1% de-activates the biological activity of endotoxin.

EXAMPLE 3

Effects of PDP on Endotoxin Activity in Bone Culture System

The test in which an endotoxin isolated from *Acintobacillus actinomycetemcomitans* Y4 (AAY4) induces the resorption of bone in a bone culture system (Kiley and Holt, *Infect. Immun.* 30:362-373, 1980) is used to assess whether PDP deactivates the bone resorptive activity of endotoxin from Y4. Fetal rat bone culture as described by Raisz, J. Clin. Invest. 44:103-116, 1965, is prepared by injecting rats with $^{45}CaCl_2$ on the 18th day of gestation. The rats are then sacrificed on the 19th day, and radii and ulnae of the embryos, with their cartilagenous ends, are removed and placed for culturing in BGJ medium (Gibco, Buffalo, N.Y.) at 37° C. with 5% $CO_2$. The medium is supplemented with 5% heated (57° C. for 3 hours) fetal calf serum. Bones are placed 4 to a well in 24 well dishes (Nunc, Gibco) containing 0.5 ml of medium per well. The release of $^{45}Ca$ into the culture media from bone incubated in the presence of a test agent is compared with the release from bones incubated in control media, and the results of bone resorption are expressed as a ratio.

Endotoxin from AAY4 is obtained from the University of Pennsylvania, School of Dentistry. AAY4 endotoxin is treated with different concentration of PDP tetrapotassium salt at 37° C. The excess PDP is removed by dialysis membrane (3500 mol. wt. maximum). This permits unreactive PDP to diffuse out while the endotoxin having molecular weight greater than 3500 is retained inside the bag. Table 3 summarizes the data.

TABLE 3

| | Treatment | No. of Rats % | $^{45}Ca$ released + S.D. | Test/ Control | Sig. |
|---|---|---|---|---|---|
| 1. | Control | 6 | 30.11 ± 1.98 | — | — |
| 2. | 10 μg/ml endotoxin Y4 AA | 6 | 85.46 ± 4.71 | 2.87 ± 0.16 | 97% compared to 1 |
| 3. | 10 μg/ml endotoxin pre-treated with 100 mcg PDP | 6 | 78.47 ± 2.9 | 2.61 ± 0.1 | not significant |
| 4. | 10 μg/ml endotoxin pre-treated with 1000 mcg PDP | 6 | 31.98 ± 4.27 | 1.06 ± 0.14 | 97% compared to 2 |

The data show that endotoxin from Y4 AA significantly induced bone resorption (compare 1 with 2) while a pre-treatment of the endotoxin with 1000 mcg/ml of PDP (0.1%) effectively inhibits the bone resorptive activity of the endotoxin.

The foregoing results in Examples 1-3 are representative of the effects of PDP tetrapotassium salt and other non-toxic water-soluble pharmaceutically acceptable PDP salts such as other alkali metal salts, alkaline earth metal salts, zinc salt and tin salt as well as $C_{1-12}$ alkyl PDP salts and other organic PDP compounds, particularly including the adenylyl, guanylyl, cytosylyl and thymylyl esters and quaternary ammonium PDP salts in inhibiting chemotaxis induced by endotoxin generated factor in serum and to inhibit endotoxin toxicity to bone in rats, rabbits and mammals in general.

We claim:

1. A method for inhibiting hypotensive shock and alveolar bone resorption caused by bacterial endotoxins which comprises introducing, into a warm blooded mammal having bone resorption by means of the oral cavity or systemically, a non-toxic water-soluble, pharmaceutically acceptable peroxydiphosphate compound, said compound being present as a salt of alkali metal, zinc, tin or quaternary ammonium or $C_{1-12}$ alkyl, adenylyl, guanylyl, cytosylyl or thymylyl ester thereby causing inactivation of said endotoxins and reducing said alveolar bone resorption and inhibiting said hypotensive shock; said peroxydiphosphate compound being present in tableted granules having a coating thereon which is not broken down during passage in the stomach of said warm blooded animal and which coating is dissolved by intestinal fluids having a pH of 5-10 when introduced in the oral cavity or being present in a solution of non-pyrogenic distilled water and sodium chloride buffered with phosphate when introduced systemically.

2. The method claimed in claim 1 wherein said peroxydiphosphate compound is present in amount of about 0.1–7% in a pharmaceutical carrier.

3. The method claimed in claim 2 wherein said contact of said peroxydiphosphate compound and said endotoxin is in a warm blooded mammalian animal and said peroxydiphosphate compound is introduced in a regimen dosage of about 0.2–14 mg/kg of body weight of said warm blooded mammalian animal.

4. The method claimed in claim 1 wherein said peroxydiphosphate compound is present as potassium salt.

5. The method claimed in claim 1 wherein said peroxydiphosphate compound is present as $C_{1-12}$ ester.

6. The method claimed in claim 1 wherein said peroxydiphosphate compound is present as adenylyl, guanylyl, cytosylyl or thylmylyl ester.

* * * * *